(12) United States Patent
Chu et al.

(10) Patent No.: US 7,161,034 B2
(45) Date of Patent: Jan. 9, 2007

(54) LIDOCAINE ANALOGS AND METHODS OF MAKING AND USING SAME

(75) Inventors: Victor P. Chu, Hockesin, DE (US); Zhu Teng, Boothwyn, PA (US); Sandra Lewisch, Bear, DE (US); Ronald L. Edwards, Bear, DE (US)

(73) Assignee: Dade Behring Inc., Deerfield, IL (US)

( * ) Notice: Subject to any disclaimer, the term of this patent is extended or adjusted under 35 U.S.C. 154(b) by 85 days.

(21) Appl. No.: 10/828,601

(22) Filed: Apr. 20, 2004

(65) Prior Publication Data

US 2005/0233398 A1    Oct. 20, 2005

(51) Int. Cl.
*C07C 233/05* (2006.01)
*A61K 31/165* (2006.01)

(52) U.S. Cl. ............ 564/153; 564/50; 564/51; 514/596; 514/597; 514/616; 436/811; 436/815; 206/569; 424/70.17

(58) Field of Classification Search ........ 564/153, 564/50, 51; 514/616, 596, 597; 206/569; 436/811, 815; 424/70.17
See application file for complete search history.

(56) References Cited

U.S. PATENT DOCUMENTS

| | | |
|---|---|---|
| 4,069,105 A | 1/1978 | Singh |
| 4,480,042 A | 10/1984 | Craig et al. |
| 4,550,075 A | 10/1985 | Bacquet et al. |
| 4,585,862 A | 4/1986 | Wang et al. |
| 4,650,771 A | 3/1987 | Buckler et al. |
| 4,785,080 A | 11/1988 | Farina et al. |
| 5,106,950 A | 4/1992 | Farina et al. |
| 5,196,351 A | 3/1993 | Harris et al. |
| 5,240,571 A | 8/1993 | Heineman et al. |
| 5,288,498 A * | 2/1994 | Stanley et al. ............ 424/440 |
| 5,354,654 A | 10/1994 | Ligler et al. |
| 5,422,281 A | 6/1995 | Harris et al. |
| 5,534,620 A | 7/1996 | Oh et al. |
| 5,705,353 A | 1/1998 | Oh et al. |
| 5,981,296 A | 11/1999 | Stout |
| 2005/0014822 A1* | 1/2005 | Defossa et al. ............ 514/485 |

OTHER PUBLICATIONS

Registry No. 107924-26-5, 1957.*
Kostowski et al, Acta Poloniae Pharmaceutica, 35(3), 379-83, 1978.*
Merck Index, 13th Edition, p. 982 (1997).

* cited by examiner

*Primary Examiner*—Shailendra Kumar
(74) *Attorney, Agent, or Firm*—Robert N. Carpenter

(57) ABSTRACT

Lidocaine analogs, latex particle-analog conjugates, and methods of making and using the same. The analogs have the formula:

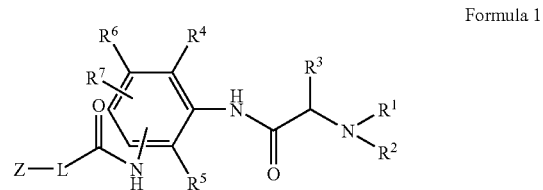

Formula 1 wherein
Z comprises a nucleophilic group and optionally a protecting group;
L is a linker;
$R^1$, $R^2$, $R^3$, $R^4$, $R^5$ are each independently H, a protecting group, or $C_1$ to $C_6$ alkyls, provided that $R^1$ and $R^3$ may form a six membered ring with the nitrogen and carbon atom to which $R^1$ and $R^3$ are attached;
$R^6$ and $R^7$ are each independently H or $C_1$ to $C_{20}$ alkyls; and including salts thereof.

The analogs are immobilized on latex particles and prepared for use in assays for lidocaine.

28 Claims, 5 Drawing Sheets

LIDOCAINE ANALOGS AND METHODS OF MAKING AND USING SAME

FIELD OF THE INVENTION

The present invention relates to novel derivatives of lidocaine. The derivatives may be used as immunogens to stimulate antibody production, or to produce particulate polymer conjugates useful in immunoassays for detection of lidocaine. The invention further relates to methods for synthesis of the lidocaine derivatives and their polymer conjugates, and to the use of the lidocaine derivates in immunoassays.

BACKGROUND OF THE INVENTION

Therapeutic drugs often require monitoring after they are administered. In many instances, the effectiveness of the drug is directly related to the concentration of the drug in the bloodstream. In such cases, the rate at which the desired blood level is achieved or exceeded will depend upon the nature of the drug, the manner of administration, the dosage, as well of the rate of metabolism. The rate at which a drug will enter the blood stream when administered other than intravenously and the rate at which the drug is metabolized varies widely with individuals. Furthermore, the level of effectiveness will also vary widely with individuals.

It is therefore desirable when administering drugs to ascertain the individual's level of effectiveness, the rate at which this level is achieved at a particular dosage and the time for which the level is maintained. In this manner, the amount of drug which is administered can then be carefully monitored to maintain the desired level. In this way, effectiveness can be assured and side effects minimized.

In order to monitor a drug in a physiological fluid, it is necessary to have sensitive tests which enable the rapid determination of the drug as distinct from any ineffectual metabolites. Thus, the test must clearly distinguish between the drug of interest and compounds of very similar structure. In competitive protein binding assays, antibodies are employed which are prepared by means of antigenic conjugates of derivatives of the drug of interest. In order for the antibodies to be effective, they must be produced in high titer, have a strong binding constant to the drug of interest, and weakly bind to have little affinity towards compounds of similar structure.

In such assays, a reagent typically provides a measurable signal related to the amount of drug present in the assay medium. Where antibodies are involved, the reagent must effectively compete with the drug for antibody binding in a reproducible manner and provide for significant changes in the signal with small changes in the drug concentration, over the concentration range of interest.

Other considerations for a reagent are that it is not affected by materials present in the unknown sample to be assayed or any interfering materials may be removed, an easily determinable signal is obtained, the reagent is stable under the assay condition and has a good storage life and the reagent is readily recognizable by the antibodies for the drug.

Lidocaine [Merck Index, 13th ed., p. 982 (1997)] was originally developed as a local anesthetic, but also possesses antiarrhythmic properties, particularly against ventricular arrhythmias. It is widely used in the treatment of post-myocardial infarction patients where it is administered by bolus injection of 1 to 2 milligrams per kilogram, followed by constant infusion at a dose level of 20 to 50 micrograms per kilogram per minute. The toxic side effects hypotension, CNS depression, and convulsions appear to be avoidable if the blood levels do not exceed 5 micrograms per milliliter (ml). On long term constant infusions, 24 to 36 hours may be required to reach a steady state. Patients receiving such therapy need to be observed carefully and continuously for signs of lidocaine toxicity. Lidocaine and possibly lidocaine metabolite blood levels may have to be determined in order to treat arrhythmias effectively and fully understand the toxicity of the drug in a given patient.

The preparation of antibodies to lidocaine and its analogs for use in immunoassays has been accomplished in the prior art by forming a particular immunogen conjugate of the drug and a conventional immunogenic carrier material and injecting such immunogen into the bloodstream of an appropriate host animal to stimulate antibody production. U.S. Pat. No. 4,069,105 describes such immunogen conjugates wherein the drug is coupled to the carrier through an imine linkage attached to one of the three unsubstituted positions on the lidocaine phenyl group. U.S. Pat. No. 4,650,771 describes derivatives wherein the drug is linked to a carrier through an aromatic methyl substituent.

While some of these prior art approaches have been effective, there continues to be a need for improvements in precise and sensitive monitoring of lidocaine.

SUMMARY OF THE INVENTION

The present invention provides novel derivatives of lidocaine that may be used as analogs for assays for lidocaine. The novel derivatives and their associated assays have been found to provide highly sensitive and precise results.

According to one aspect of the invention, lidocaine analogs are provided having the formula:

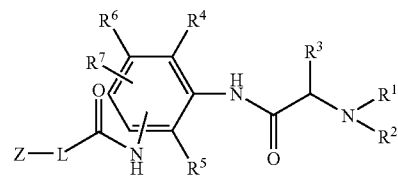

wherein
Z comprises a nucleophilic group and optionally a protecting group;
L is a linker;
$R^1$, $R^2$, $R^3$, $R^4$, $R^5$ are each independently H, a protecting group, or $C_1$ to $C_6$ alkyls, provided that $R^1$ and $R^3$ may form a six membered ring with the nitrogen and carbon atom to which $R^1$ and $R^3$ are attached; and
$R^6$ and $R^7$ are each independently H or $C_1$ to $C_{20}$ alkyls; and including salts thereof.

According to another aspect of the present invention, a composition for use in immunoassays is provided. The composition has the formula:

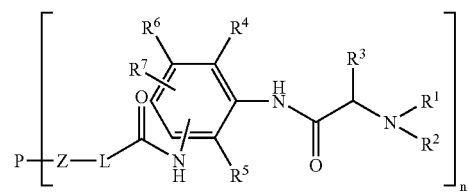

wherein:
P is a latex polymer having at least one functional group;
Z is a nucleophilic group capable of coupling with the functional group;

L is a linker;

n is an integer from 1 to about 100,000;

$R^1$, $R^2$, $R^3$, $R^4$, $R^5$ are each independently H, a protecting group, or $C_1$ to $C_6$ alkyls, provided that $R^1$ and $R^3$ may form a six membered ring with the nitrogen and carbon atom to which $R^1$ and $R^3$ are attached, and $R^6$ and $R^7$ are each independently H or $C_1$ to $C_{20}$ alkyls.

According to another aspect of the invention, the compositions according to the present invention are used in the determination of the amount or presence of lidocaine in a sample, and may be included in kits for that purpose.

The foregoing aspects of the invention are illustrative of those that can be achieved by the present invention and are not intended to be exhaustive or limiting of the possible advantages which can be realized. Thus, these and other aspects of the invention will be apparent from the description herein or can be learned from practicing the invention, both as embodied herein or as modified in view of any variation which may be apparent to those skilled in the art. Accordingly, the present invention resides in the novel methods, arrangements, combinations and improvements herein shown and described.

DETAILED DESCRIPTION OF THE PREFERRED EMBODIMENTS

Figure 1:
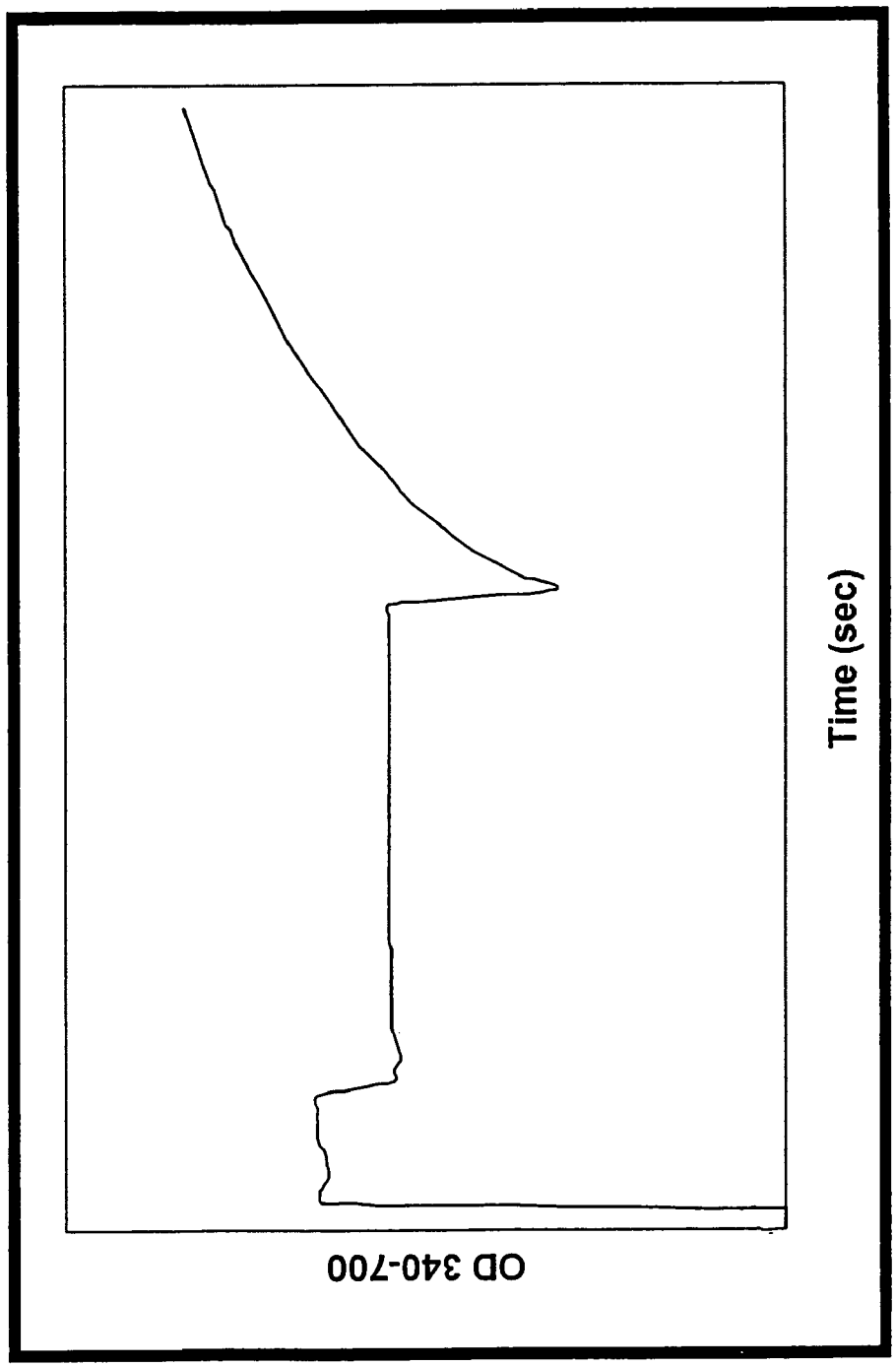
FIG. 1 shows a typical plot of optical density (at 340–700 nm) versus time for the PETINIA assays according to one aspect of the present invention.

The novel lidocaine analogs of the present invention have the formula:

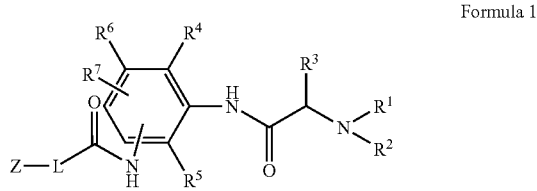

Formula 1

The substitutents $R^1$, $R^2$, $R^3$, $R^4$, and $R^5$ are each independently H, a protecting group, or $C_1$ to $C_6$ alkyls. $R^3$ represents one or two substitutions on the associated carbon atom, which may be the same or different substituents. Furthermore, $R^1$ and $R^3$ may be taken together to form a six membered ring with the nitrogen and carbon atoms to which $R^1$ and $R^3$ are respectively attached. In one particular embodiment of the invention, R1 and R2 are ethyl; R3 is H; and R4 and R5 are methyl.

R6 and R7 are each independently H, a protecting group, or a C1 to C20 alkyl. In one particular embodiment, R6 and R7 are C1 to C6 alkyls, and in another particular embodiment, R6 and R7 are H. R7 may be located at the meta or para position, and the linker L located at the other position. In one embodiment, $R^7$ is para and L is meta.

Z comprises a nucleophilic group and optionally a protecting groups. Suitable nucleophilic substituents includes tertiary amines, secondary amines, primary amines, —SH, and —OH. As will be explained below, the nucleophilic group is selected to allow coupling with a functional group on a carrier, such as a latex polymer. Suitable protecting groups include t-butoxycarbonyl and other conventional protecting groups known to those skilled in the art.

L is a linking group having a skeleton of 1 to about 20 carbon atoms. The linking group L may also include from 0 to about 10 heteroatoms, such as nitrogen, oxygen, and sulfur. In one embodiment, L is a linking group —X—NC(=O)—Y—, wherein X and Y are independently a bond or 1 to 20 carbon atoms. Either of X or Y may be coupled to Z. X and Y may also contain from 0 to 10 heteroatoms. X and Y are preferably selected from the group consisting of alkyls, amidos, carbonyls, and thioethers. In one preferred embodiment, the linking group L comprises a straight chain.

The compounds of the invention also encompass the salts of Formula 1. In one embodiment of the invention, the compounds are provided in their acid salt form.

According to one embodiment of the invention, the compounds of Formula 1 may be synthesized by first preparing aminolidocaine or a derivative thereof from lidocaine or a lidocaine derivative. The amino substituent of the aminolidocaine derivative is then coupled to a linker group L and nuclephilic group Z using suitable reagents. In one embodiment of the invention, one of the reagents is a derivative of Z-L.

In one embodiment of the invention, suitable reagents include t-butoxycarbonyl (t-BOC) compounds, many of which are commercially available. The t-BOC group as a protecting group for the nucloephilic group Z during the addition of the Z-L derivative to the amino group of the aminolidocaine derivative. Deprotection with an acid yields compounds of Formula 1. Those skilled in the art will recognize that other linkers and protecting groups could be provided to synthesize the compounds of Formula 1, as well as other synthetic strategies. For example, the Z and L components may be added separately. The following Examples illustrate particular embodiments of the present invention:

LIDOCAINE ANALOG SYNTHESIS EXAMPLE 1

The intermediate Formula 2 (aminolidocaine) was prepared using the synthetic route outlined in Scheme I.

Scheme I:

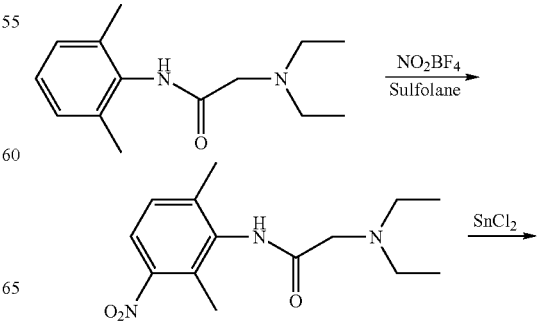

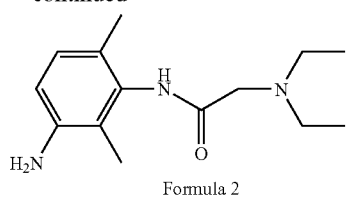

As shown in Scheme II, Formula 2 was first treated with 3 equiv. of 1,1'-Carbonyl Diimidazole (CDI) in acetonitrile to afford Formula 3. Next, 3.2 equiv. of Formula 4 (t-BOCNH(CH$_2$)$_6$NH$_2$) was added in situ to the above reaction solution to yield 62% of Formula 5. After deprotection with trifluoroacetic acid, Formula 6 was obtained in 48% yield. Treatment of Formula 6 with base gave Formula 7 in quantitative yield.

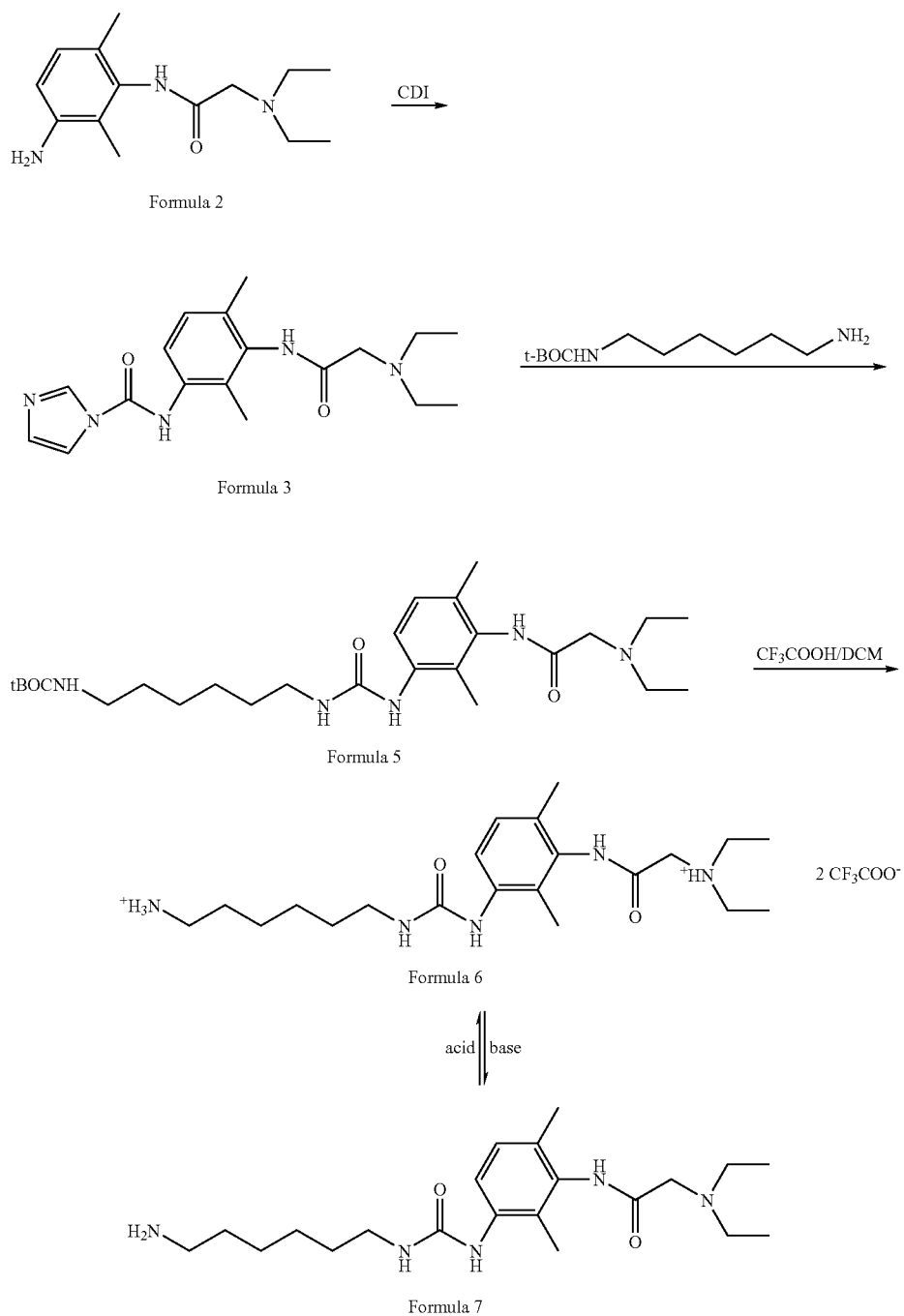

LIDOCAINE ANALOG SYNTHESIS
EXAMPLE 2

In Scheme III, a protected bi-functional hydrophilic linker, Formula 8 (t-BOC-AA-14), was treated with 1.2 equiv. of (EtO)$_2$POCl and triethylamine in THF to activate the carboxyl group by formation of an acid chloride as an intermediate. This was then reacted with 1.0 equiv. of Formula 2 in situ. The coupled Formula 9 was obtained in 50% yield after purification by column chromatography. Deprotection of Formula 9 with trifluoroacetic acid gave Formula 10 in 95% yield. Treatment of Formula 10 with base gave Formula 11 in quantitative yield.

binding pair having a first and second specific member, such as the lidocaine analog of the present invention conjugated to a carrier and an antibody specific for lidocaine and the conjugate. The antibodies may be raised by conventional techniques, for example, injection of the immunogen into a mouse, rabbit or sheep, and may be screened by known methods, and evaluating properties such as specificity, conjugate inhibition, curve size and cross-reactivity. The obtained antibody is spiked into the antibody diluent to prepare the antibody reagent. Suitable anti-lidocaine antibodies are manufactured as part of the EMIT® Lidocaine Assay by Dade Behring, Inc. of Deerfield, Ill.

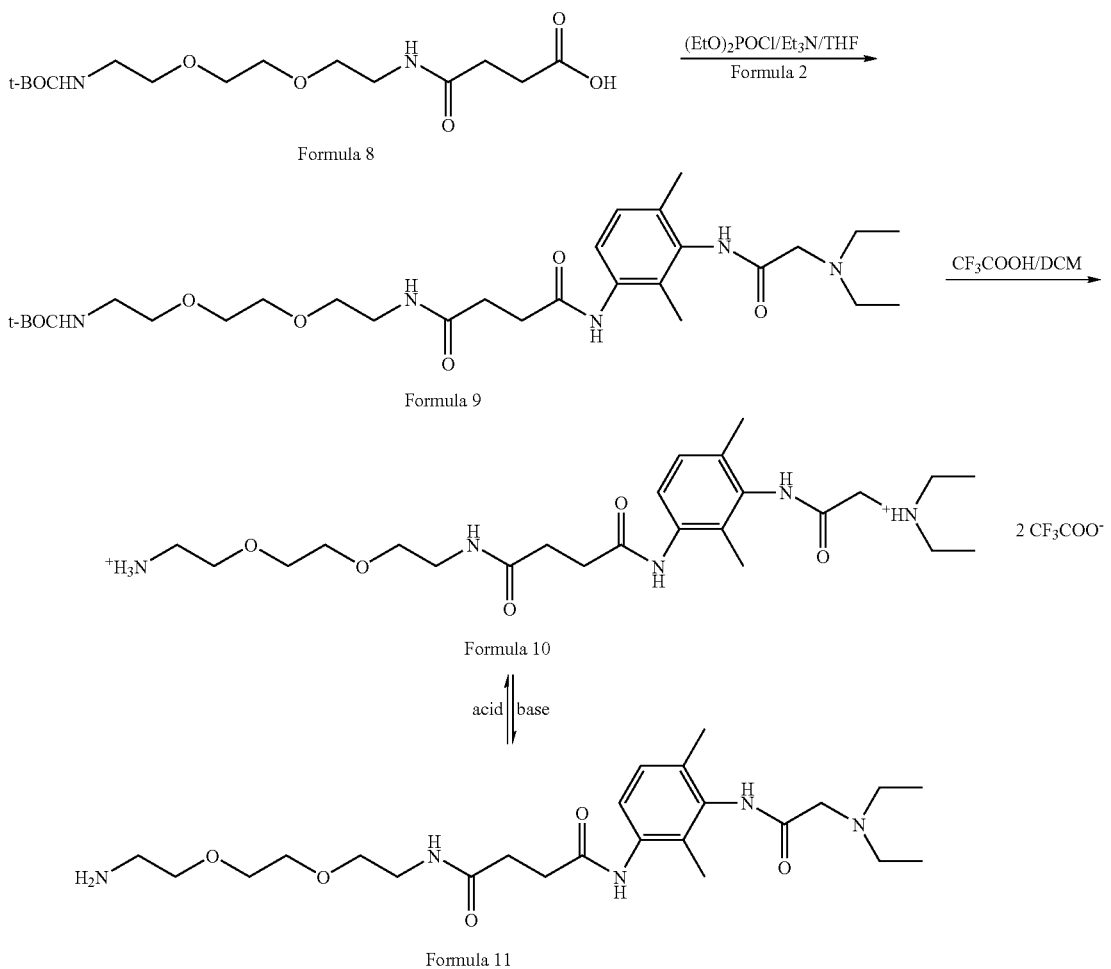

The novel compounds of the present may be used in variety of assays for the determination of lidocaine and analogs of lidocaine. In particular, the lidocaine analogs are suited for use in immunoassays in which they act as a member of a specific binding pair. The lidocaine analogs bind selectively to antibodies generated against lidocaine. The novel compounds may be used in a number of immunoassay formats, including both heterogenous and homogenous assays, radioimmunoassays, enzyme-based immunoassays, and luminescence assays, etc.

In one embodiment of the invention, a sample suspected of containing lidocaine is placed in contact with a specific The lidocaine analog and lidocaine compete for the antibodies. In the absence of lidocaine, the lidocaine analog conjugate forms a complex with the antibodies. The extent of complex formed is a function of the amount of lidocaine present. In this manner, the presence or amount of lidocaine can be determined by measuring the extent of complex formation.

In one embodiment of the invention, the lidocaine analogs are used as immunogens in a turbidmetric assay. In one particularly preferred embodiment, the lidocaine analogs are used Particle Enhanced Turbidimetric Inhibition Immunoassay (PETINIA). This immunoassay format uses drug-hydrophilic linker-particle reporter reagents (particle reagents). These particle reagents utilize very small latex particles (e.g., 70 nm) to which have been attached a drug or other compound of interest. When viewed with monochromatic light having a wavelength (e.g., 340 nm) larger than the diameter of the suspended particles, the suspension is relatively transparent. Under optimal conditions, addition of antibody specific for the drug on the particles will cause the particles to agglutinate, forming insoluble complexes. These complexes cause the suspension to become turbid and scatter light. When an antibody is added to a sample containing drug/particle conjugates and free drug, free drug competes with particle-bound drug for antibody, thereby inhibiting both the rate and extent of agglutination. This provides the basis for quantifying the amount of drug in the sample. Specifically, in the present invention, lidocaine-particle reagents and anti-lidocaine antibodies enable a rapid, precise and accurate PETINIA method for determining the amount of lidocaine present in biological fluids. Such methods, by enhancing the rate, size, and extent of the immune complex formation, provide more efficient and effective immunoassays for determining the concentration of medically important pharmacological agents, such as lidocaine. The present invention provides reagents and methods for conducting such improved immunoassays.

Non-specific agglutination (agglutination in the absence of antibody) of the latex-antigen conjugates is thought to be prevented due to electrostatic repulsion between similarly-charged conjugates, and steric repulsion of bound surface components (the antigens or antigen analogues). Upon reaction of these groups with antibodies, the charge of the latex-bound moieties is altered, resulting in the formation of insoluble complexes. Accumulation of these complexes in the reaction solution will increase the amount of light scattered when the reaction chamber is illuminated, the extent of which can be monitored by turbidimetry. The assay buffer used in this reaction must be optimized to prevent non-specific reactions from occurring, which may affect particle stability and utility of the assay. The buffer is optimized in order to manage the shape of the calibration curve and determine the concentration range of analyte detection.

When a sample containing free antigen (also referred to as an analyte) is present in the reaction solution, competition for the antibody occurs between the bound antigen or antigen analogue in the particle conjugate and the analyte. This results in an inhibition of the formation of insoluble aggregated complexes and therefore an inhibition of the increase in turbidity. This inhibition can be calibrated by addition of known concentrations of analyte, enabling determination of analyte concentration in various samples.

According to another aspect of the invention, a composition is provided for use in immunoassays, such as in PETINIA. The composition has the formula:

Formula 12

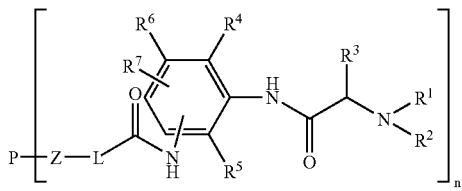

The substitutents $R^1$ through $R^7$, L and Z are defined in the manner as described above for Formula 1. P is a latex polymer having at least one functional group on the surface thereof capable of coupling with the nucleophilic group of Z. Such functional groups include alkoxysilyl; activated carboxyl; chloro or bromo methylphenyl. A particularly preferred functional group is an epoxy group. A particularly useful polymer is a polystyrene latex polymer having a polystyrene core, with a glycidyl methacrylate polymer or copolymer as a shell. Such polymers are described in U.S. Pat. No. 4,480,042. Lidocaine analogs may be directly reacted with polystyrene/glycidyl methacrylate core/shell particles, binding the conjugates by reaction between the aliphatic amino group on the analogs and the reactive epoxide rings. Particles having styrene-butadiene latex cores and shells containing glycidyl methacrylate monomers or hydroxyalkyl methacrylate ester monomers are also suitable.

The number (n) of analog moieties per latex particle is preferably from 1 to about 100,000, preferably from about 100 to 20,000, and more preferably, from about 1000 to 10,000.

The methods of preparation of the compositions of Formula 12 are illustrated in the following Examples:

PARTICLE REAGENT PREPARATION
EXAMPLE 1

Lidocaine analog-particle reagents of various level of immobilization of Formula 11 were prepared by dropwise and sequential addition of: GAFAC (0.266–0.300 mL, 14.7% stock solution, 0.7% in reaction), Formula 11 (0.281–0.949 mL, 40 mM stock solution; 2, 4, and 6 mM in reaction), and DA-10 (0.052–0.058 mL, 324 mM stock solution, 3 mM in reaction) into diafiltered particle raw material (5 mL, 10.3% stock solution, 9.23–8.20% solids in reaction), while pH was measured and adjusted to 9.2. The reactions were carried out at 70° C. for 18 hours. Each supernatant and additional wash buffer (10 mL) was separated by centrifugation (28,000 rpm) and decanting. Fresh wash buffer (20 mL, 1.0% GAFAC, 15 mM phosphate buffer, 0.2% Proclin, 0.006% neomycin sulfate) was added to each reaction tube and the particle reagents resuspended by sonication. This supernatant exchange process is repeated 3 more times. The final pellets were resuspended into wash buffer (10 mL) resulting in particle concentrate solutions (10 mL, 50 mg/mL).

PARTICLE REAGENT PREPARATION
EXAMPLE 2

Lidocaine analog-particle reagents of various level of immobilization of Formula 7 were prepared by dropwise and sequential addition of: GAFAC (0.510–0.526 mL, 14.7% stock solution, 0.7% in reaction), Formula 7 (0.101–0.417 mL, 159 mM stock solution; 1.5, 3, 4, and 6 mM in reaction), and DA-10 (0.099–0.102 mL, 324 mM stock solution, 3 mM in reaction) into diafiltered particle raw material (10 mL, 10.3% stock solution, 9.65–9.36% solids in reaction), while pH was measured and adjusted to 9.2. The reactions were carried out at 70° C. for 18 hours. Each supernatant and additional wash buffer (10 mL) was separated by centrifugation (28,000 rpm) and decanting. Fresh wash buffer (20 mL, 1.0% GAFAC, 15 mM phosphate buffer, 0.2% Proclin, 0.006% neomycin sulfate) was added to each reaction tube and the particle reagents resuspended by sonication. This supernatant exchange process was repeated 3 more times. The final pellets are resuspended into wash buffer (20 mL) resulting in particle concentrate solutions (20 mL, 50 mg/mL).

PARTICLE REAGENT PREPARATION
EXAMPLE 3

Lidocaine analog-particle reagents of various level of immobilization of native lidocaine were prepared by dropwise and sequential addition of: GAFAC (0.507–0.513 mL, 14.7% stock solution, 0.7% in reaction), lidocaine (0.043–0.175 mL, 369 mM stock solution; 1.5, 3, 4, and 6 mM in reaction), and DA-10 (0.098–0.100 mL, 324 mM stock solution, 3 mM in reaction) into diafiltered particle raw material (10 mL, 10.3% stock solution, 9.71–9.58% solids in reaction). The pH was measured and adjusted to 9.2. The reactions were carried out at 70° C. for 18 hours. Each supernatant and additional wash buffer (10 mL) was separated by centrifugation (28,000 rpm) and decanting. Fresh wash buffer (20 mL, 1.0% GAFAC, 15 mM phosphate buffer, 0.2% Proclin, 0.006% neomycin sulfate) was added to each reaction tube and the particle reagents resuspended by sonication. This supernatant exchange process is repeated 3 more times. The final pellets were resuspended into wash buffer (20 mL) resulting in particle concentrate solutions (20 mL, 50 mg/mL).

According to one particular embodiment of the invention, a PETINIA based assay for lidocaine is conducted as follows. A measure of absorbance $r_0$ ($\lambda$=340–700 nm) in an empty sample cuvette is taken at time $t_0$ (e.g., 0 sec.) and used as a control value. A known volume of a particle reagent having a defined concentration of particle/lidocaine analog conjugate is added to the sample cuvette at time $t_1$ (e.g., 16 sec.), resulting in a solution having a known volume $v_0$. An increased absorbance occurs upon addition of particle reagent. Generally 340 nm is the wavelength of choice because the complex absorbs maximally at that wavelength. At this point $t_2$ (e.g., 66 sec.), a known volume of a sample solution suspected of containing lidocaine is added to the sample cuvette, increasing the solution volume to a volume $v_1$. Absorbance $r_1$ at a wavelength of 340–700 nm is then recorded at a time $t_3$ (e.g., 102 sec.), and a second absorbance $r_2$ is recorded at a second, later, time $t_4$ (e.g., 252 sec.). The absorbance at 700 nm is observed to subtract background noise to normalize the readings. Certain other wavelengths as known to the skilled in the art may also be used. The difference between these values at 340 nm ($r_2-r_1$) provides a good measure of the presence of nonspecific binding between the sample and the particle reagent in the test solution; if this difference is greater than 50 mAU, the particle reagent may have agglutinated in the absence of antibody, and the results of the test may be unreliable.

A known quantity of antibody reagent is then added to the test solution at time $t_5$ (e.g., 282 sec.), increasing the solution volume to a volume $v_3$. The absorbance undergoes an initial decrease due to the increase in the solution volume; next, the absorbance undergoes a gradual increase as the antibody reacts with the antigen particles, resulting in a formation of insoluble aggregated complexes. Any free antigen in the sample solution will compete competitively with the particle-bound antigen analogs, antigen particles for the available antibody, resulting in measurable inhibition of the increase in turbidity. Thus, the rate at which turbidity increases is dependent on the concentration of analyte present. At a later time, $t_6$ (e.g., 438 sec.), absorbance $r_3$ is measured. Note that the specific time values and wavelengths provided here are exemplary only; a person skilled in the art will recognize that different values may also be used with success.

This absorbance data may then be used to obtain information about the rate of particle agglutination. This rate is affected by competition for antibodies between the lidocaine in solution and the particle-bound lidocaine analog. This competition leads to a reduction in the rate of particle agglutination. Under the assumption that changes in the rate of particle agglutination are dependent on the concentration of free lidocaine in solution, agglutination rates may be used to derive the concentration of free lidocaine in solution. This rate data may be calculated using the following equation (Equation 1):

$$\text{Rate} = r_3 - ((v_1/v_3)*r_2) - ((1-v_1/v_3)*r_0) \quad \text{(Equation 1)}$$

In the above equation, $(v_1/v_3)$ is the ratio of the solution volume at the time absorbance measurement $r_1$ is taken to the solution volume at the time absorbance measurement $r_3$ is taken. By analyzing several known concentrations of lidocaine in solution, a standard curve can be generated. From this curve, the rate calculated from the analysis of an unknown sample can then be directly translated into a lidocaine concentration via some typical curve fitting algorithm, such as a Logit fit. FIG. 1 illustrates a typical absorbance curve generated from this method.

The following precautions should be taken in using this method. If the difference between $r_2$ and $r_0$ at 340 nm is greater than 1700 mAU, and/or the difference between $r_2$ and $r_0$ at 700 nm is greater than 100 mAU, the reaction solution in the cuvette may contain foam, causing the results to be of dubious value. If $r_1-r_0<350$ mAU, insufficient particle reagent may have been delivered to the cuvette. If $r_2-r_1>50$ mAU, there may be particle agglutination in the absence of antibody (or non-specific agglutination). If the Final Optical Density (FOD) at 340 nm exceeds 1700 mAU, the absorbance of the solution is above the linear response region and possibly the detection limit of the analyzer. The results of the PETINIA assay may then have an unacceptable linearity response, and should be rejected.

This immunoassay protocol is illustrated in the Examples that follow:

IMMUNOASSAY EXAMPLE 1

The following reagents were prepared:

Particle reagent. The particles described in the Particle Reagent Preparation Example 1 above (with a loading of 2.0 mM) were diluted to a concentration of 3.0 mg/mL in Particle Wash Buffer (1.0% GAFAC, 15 mM Phosphate, 0.2% Proclin 300 and 0.006% Neomycin Sulfate (pH 7.8).

Antibody Reagent. Anti-lidocaine monoclonal antibodies were diluted to a concentration of 190 µg/mL in dilution buffer (150 mM Phosphate, 0.216% GAFAC, 0.002% Thimerosal (pH 7.72).

Assay Buffer. 150 mM Phosphate, 2% polyethylene glycol 8000, 0.216% GAFAC, 0.002% Thimerosal (pH 7.72).

An assay was carried out on a Dimension® clinical chemistry system from Dade Behring Inc, Deerfield, Ill., using a sample solution containing free lidocaine. At time t=0 sec., the absorbance $r_0$ of an empty cuvette at 340–700 nm was measured as a control air blank. At time t=57.6 sec., 80 µl PR and 130 µl of assay buffer followed by 103 µl of water were added to the cuvette. At time t=1.20 min, 6 µl of sample followed by 32 µl of water were added to the cuvette. Later, at time t=1.72 min, the absorbance $r_1$ of the test solution was recorded at a total solution volume $v_1$ of 351 µl. A second absorbance $r_2$ was recorded at time t=4.28 min. The difference between $r_2$ and $r_1$ was found to be less than 50 mAU; therefore, the risk of particle agglutination from excessive non-specific binding was deemed to be acceptable. Thus, at time t=284.8 sec., 80 µl of AR followed by 40 µl of water was added to the test solution. Finally, at time t=4.86 min, the absorbance $r_3$ of the test solution was recorded at a final solution volume $v_3$ of 351 µl.

Figure 2:
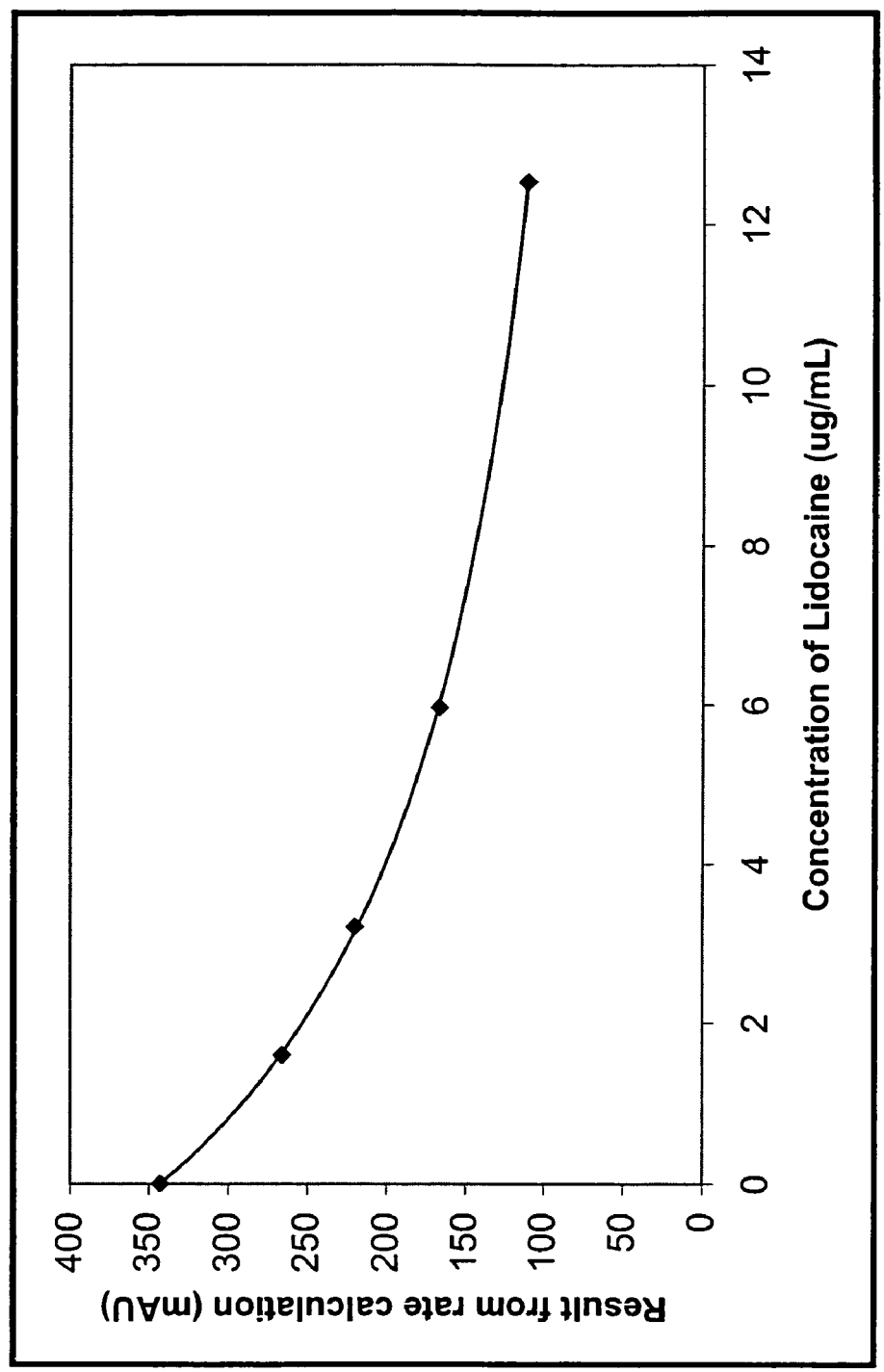
FIG. 2 shows a standard curve for a PETINIA assay according to the Immunoassay Example 1.

The procedure described above for determination of rate values was applied to multiple sample solutions having known lidocaine concentrations. For each solution, values correlating to the rate of particle agglutination were plotted in FIG. 2. A logit curve fitting was used to generate a standard curve, as shown in FIG. 2.

The effectiveness of the PETINIA assay as described above was then verified by comparing the results of PETINIA assays to the commonly used EMIT® Lidocaine Assay (Enzyme Multiplied Immunoassay). The EMIT® Lidocaine Assay was performed on an aca® discrete clinical analyzer from Dade Behring Inc., Deerfield, Ill., according to the established specifications. A number of samples containing lidocaine were then tested by the EMIT® method. The same set of samples was then retested, using the PETINIA assay technique described above. The results of the tests are summarized in Table I.

TABLE I

Comparison of Measured Lidocaine Samples

| Lidocaine Concentration (ug/ml) | PETINIA Method (ug/ml) | EMIT ® Lidocaine Assay (ug/ml) |
|---|---|---|
| 0.0 | 0.1 | 0.0 |
| 0.5 | 0.6 | 0.4 |
| 1.0 | 1.0 | 0.7 |
| 1.5 | 1.5 | 1.2 |
| 2.0 | 2.2 | 2.0 |
| 2.5 | 2.4 | 2.2 |
| 3.0 | 2.8 | 2.6 |
| 3.5 | 3.2 | 2.9 |
| 4.0 | 3.4 | 3.2 |
| 4.5 | 3.9 | 3.7 |
| 5.0 | 4.9 | 4.2 |
| 5.5 | 4.8 | 4.3 |
| 6.0 | 5.1 | 4.6 |
| 6.5 | 6.2 | 5.4 |
| 7.0 | 6.6 | 6.0 |
| 7.5 | 7.0 | 6.2 |
| 8.0 | 6.9 | 6.4 |
| 9.0 | 8.0 | 6.9 |
| 10.0 | 9.3 | 8.2 |
| 11.5 | 11.5 | 11.0 |

Figure 3:
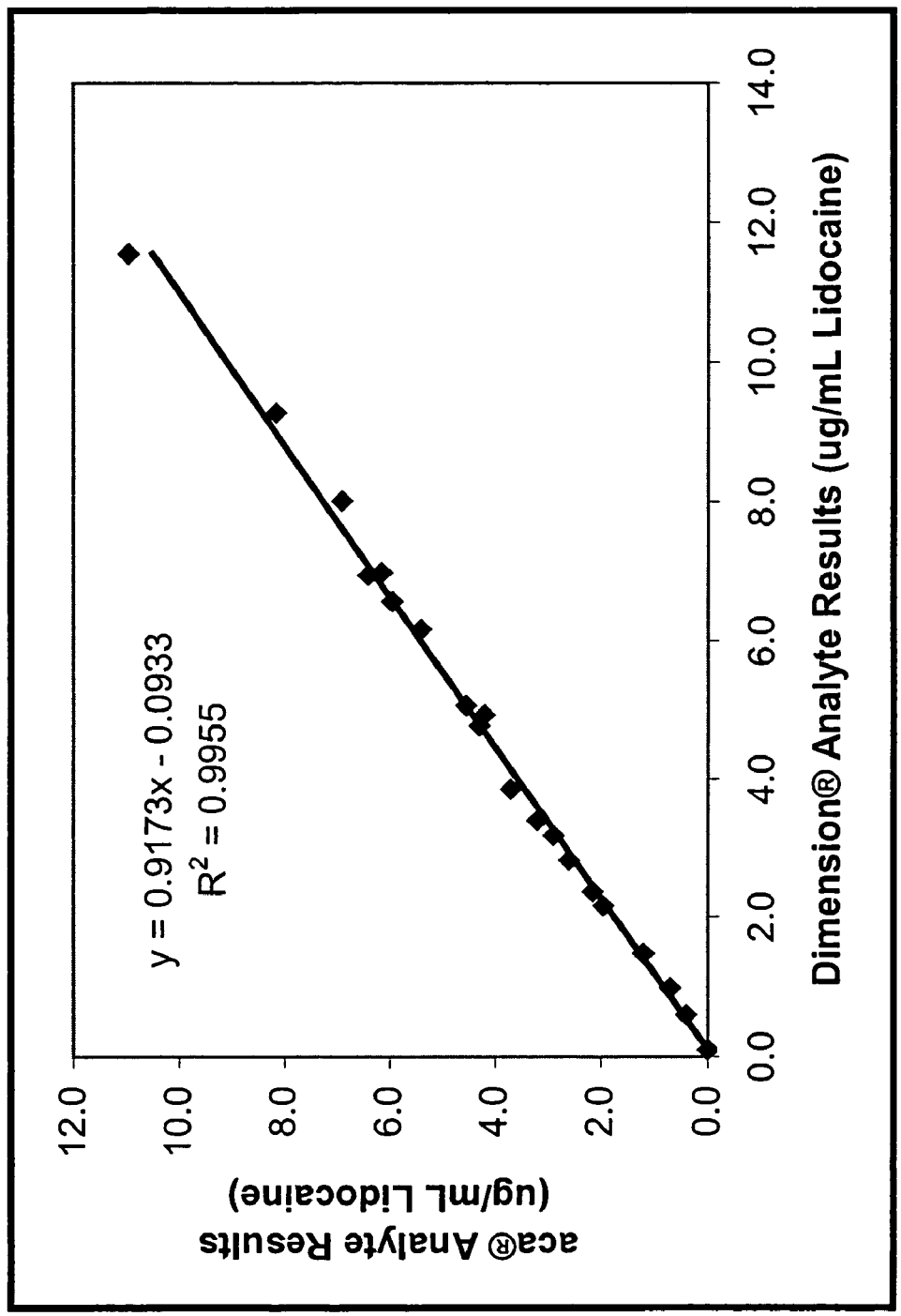
FIG. 3 shows a correlation of the concentration data derived from a commercially available assay to the concentration data derived from a PETINIA assay in Immunoassay Example 1.

To determine how well the values derived from the two methods correlate, the concentrations from the EMIT® data from the aca® analyzer were plotted against the concentrations from the PETINIA data (FIG. 3). The result was a straight line having a slope of 0.9713, and a y-intercept of 0.0933. The R squared value was 0.9955, the ideal value of 1.00. These results demonstrate that the two methods produce results that correlate well.

IMMUNOASSAY EXAMPLE 2

Particle Reagent: The particles described in the Particle Reagent Preparation Example 2 above (with a loading of 6.0 mM) were diluted to a concentration of 5.0 mg/mL in Particle Wash Buffer (1.0% GAFAC, 15 mM Phosphate, 0.2% Proclin 300 and 0.006% Neomycin Sulfate (pH 7.8)).

Antibody Reagent: Anti-lidocaine monoclonal antibodies were diluted to a concentration of 190 µg/mL in dilution buffer (200 mM Borate, 400 mM NaCl, 1.0% GAFAC, 0.2% Proclin (pH 7.9)).

Assay Buffer: 200 mM Borate, 400 mM NaCl, 2% polyethylene glycol 8000, 1.0% GAFAC, 0.2% Proclin (pH 7.9)

This assay was also carried out on a Dimension® clinical chemistry system from Dade Behring Inc, Deerfield, Ill., using a sample solution containing free lidocaine. At time t=0 sec., the absorbance $r_0$ of an empty cuvette at 340–700 nm was measured as a control air blank. At time t=57.6 sec., 80 µl PR and 130 µl of assay buffer followed by 103 µl of water were added to the cuvette. At time t=1.20 min, 6 µl of sample followed by 32 µl of water were added to the cuvette. Later, at time t=1.72 min, the absorbance $r_1$ of the test solution was recorded at a total solution volume $v_1$ of 351 µl. A second absorbance $r_2$ was recorded at time t=4.28 min. The difference between $r_2$ and $r_1$ was found to be less than 50 mAU; therefore, the risk of particle agglutination from excessive non-specific binding was deemed to be acceptable. Thus, at time t=284.8 sec., 80 µl of AR followed by 40 µl of water was added to the test solution. Finally, at time t=4.86 min, the absorbance $r_3$ of the test solution was recorded at a final solution volume $v_3$ of 351 µl.

Figure 4:
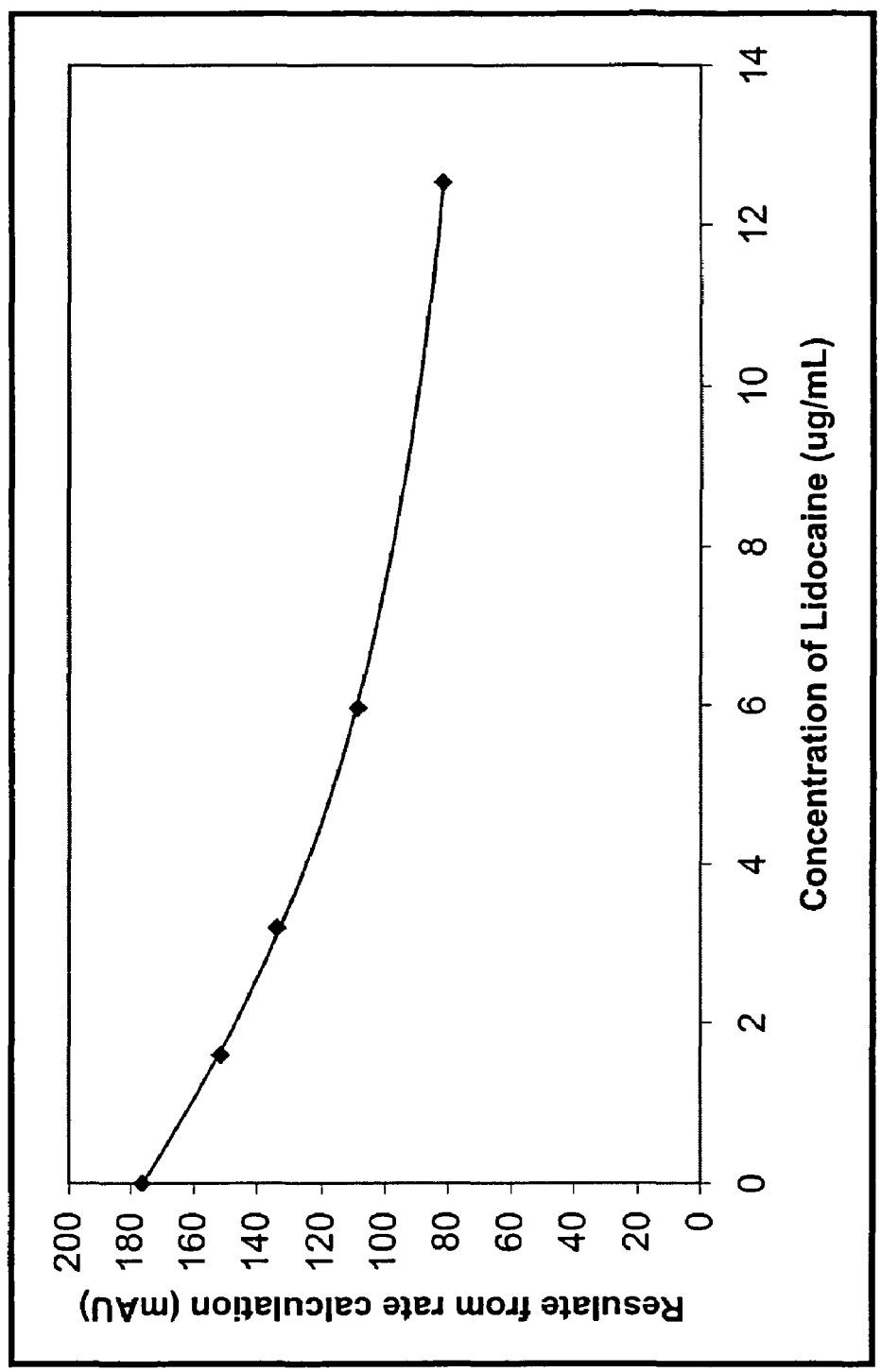
FIG. 4 shows a standard curve for a PETINIA assay according to the Immunoassay Example 2.

The procedure described above for determination of rate values was applied to multiple sample solutions having known lidocaine concentrations. For each solution, values correlating to the rate of particle agglutination were plotted in FIG. 4. A logit curve fitting was used to generate a standard curve, as shown in FIG. 4.

The effectiveness of the PETINIA assay as described above was also verified by comparing the results of PETINIA assays to the commonly used EMIT® Lidocaine Assay (Enzyme Multiplied Immunoassay). The EMIT® Lidocaine Assay was performed on an aca® discrete clinical analyzer from Dade Behring Inc., Deerfield, Ill., according to the established specifications. A number of samples believed to contain lidocaine were then tested by the EMIT® method. The same set of samples was then retested, using the PETINIA assay technique described above. The results of the tests are summarized in Table II.

TABLE II

Comparison of Measured Lidocaine Samples

| Lidocaine Concentration (ug/ml) | PETINIA Method (ug/ml) | EMIT ® Lidocaine Assay (ug/ml) |
|---|---|---|
| 0.0 | 0.4 | 0.0 |
| 0.5 | 0.8 | 0.4 |
| 1.0 | 1.0 | 0.7 |
| 1.5 | 1.4 | 1.2 |
| 2.0 | 2.1 | 2.0 |
| 2.5 | 2.3 | 2.2 |
| 3.0 | 2.9 | 2.6 |
| 3.5 | 3.2 | 2.9 |
| 4.0 | 3.3 | 3.2 |
| 4.5 | 3.9 | 3.7 |
| 5.0 | 4.5 | 4.2 |

TABLE II-continued

Comparison of Measured Lidocaine Samples

| Lidocaine Concentration (ug/ml) | PETINIA Method (ug/ml) | EMIT ® Lidocaine Assay (ug/ml) |
|---|---|---|
| 5.5 | 4.3 | 4.3 |
| 6.0 | 4.7 | 4.6 |
| 6.5 | 5.9 | 5.4 |
| 7.0 | 6.5 | 6.0 |
| 7.5 | 6.6 | 6.2 |
| 8.0 | 6.4 | 6.4 |
| 9.0 | 7.2 | 6.9 |
| 10.0 | 8.4 | 8.2 |
| 11.5 | 10.9 | 11.0 |

Figure 5:
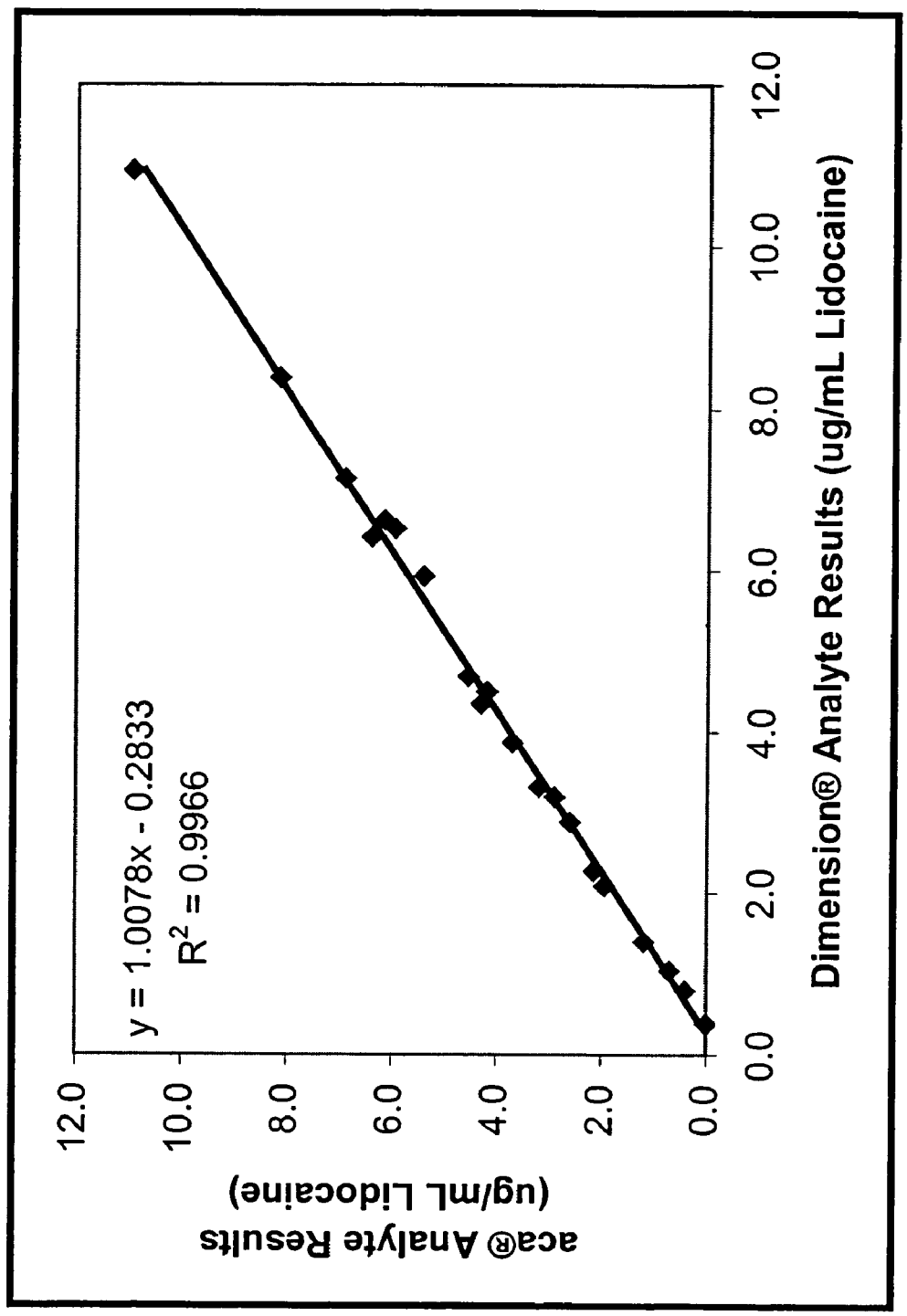
FIG. 5 shows a correlation of the concentration data derived from a commercially available assay to the concentration data derived from a PETINIA assay in Immunoassay Example 2.

To determine how well the values derived from the two methods correlate, the concentrations from the EMIT® data from the aca® analyzer were plotted against the concentrations from the PETINIA data (FIG. 5). The result was a straight line having a slope of 1.0078, and a y-intercept of 0.2833. The R-squared value was 0.9966, the ideal value of 1.00. These results demonstrate that the two methods produce results that correlate well.

According to another aspect of the invention, a kit is provided for use in performing immunoassays. The kit may includes reagents packaged in combination, in the same or separate containers, in liquid or lyophilized form so that the ratio of the reagents provides for substantial optimization of the method and assay. The reagents can be combined in one or more containers depending on the cross-reactivity and stability of the reagents. The kit may also include written instructions of a method in accordance with the present invention as described above.

The reagents for the kit will generally include the conjugates of the present invention and an antibody that binds specifically with the conjugates and with lidocaine or a derivative thereof. The antibodies may be raised, by conventional techniques, against the conjugates or against lidocaine or a derivative thereof.

The kit may also include other suitable materials, such as an assay buffer, or other ancillary reagents, such as stabilizers and the like. The kit may be used in a variety of immunoassay formats. In one embodiment of the invention, the kit is used for performing PETINIA assays as described above.

It should be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention.

Accordingly, while the present invention has been described herein in detail in relation to specific embodiments, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

What is claimed is:

1. A compound of the formula:

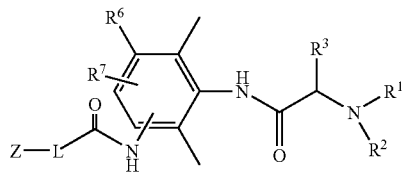

wherein
Z is a nucleophilic group and optionally a protecting group;
L is a linker;
$R^1$, $R^2$, $R^3$ are each independently H, a protecting group or $C_1$ to $C_6$ alkyls, provided that $R^1$ and $R^3$ may form a six membered ring with the nitrogen and carbon atom to which $R^1$ and $R^3$ are attached; and $R^6$ and $R^7$ are each independently H or $C_1$ to $C_{20}$ alkyls;
or a salt thereof.

2. The compound of claim 1, wherein Z is selected from the group consisting of a tertiary amine, a secondary amine, a primary amine, —SH, and —OH.

3. The compound of claim 1, wherein Z is a tertiary amine.

4. The composition of claim 1, wherein L is a 1 to 20 carbon skeleton having 0 to 10 heteroatoms.

5. The compound of claim 1, wherein L is —NC(=O)—Y—
wherein Y is a 1 to 20 carbon skeleton having 0 to 10 heteroatoms.

6. The compound of claim 1, wherein L is a straight chain.

7. The compound of claim 5, wherein Y is selected from the group consisting of alkyls, amidos, carbonyls, ethers, and thioethers.

8. The compound of claim 1, wherein $R^7$ is in the para position.

9. The compound of claim 8, wherein $R^6$ and $R^7$ are each independently H or $C_1$ to $C_6$.

10. The compound of claim 8, wherein $R^1$ and $R^2$ are each ethyl, and $R^3$ is H.

11. The compound of claim 10, wherein $R^6$ and $R^7$ are each H.

12. The compound of the formula

Formula 7

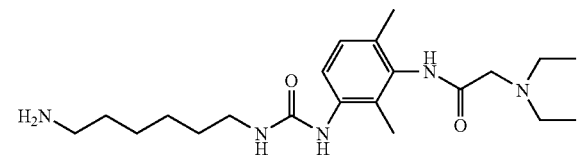

or a salt thereof.

13. The compound of the formula:

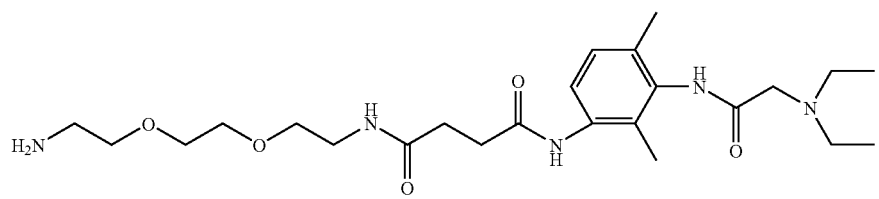

Formula 11 or a salt thereof.

14. A composition of the formula:

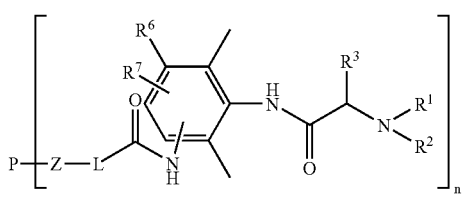

wherein:
- Z is a nucleophilic group and optionally a protecting group;
- P is a latex polymer having at least one functional group capable of coupling with the nucleophilic group;
- L is a linker;
- n is an integer from 1 to about 100,000;
- $R^1$, $R^2$, $R^3$ are each independently H, a protecting group or $C_1$ to $C_6$ alkyls, provided that $R^1$ and $R^3$ may form a six membered ring with the nitrogen and carbon atom to which $R^1$ and $R^3$ are attached; and
- and $R^6$ and $R^7$ are each independently H or $C_1$ to $C_{20}$ alkyls.

15. The composition of claim 14, wherein $R^7$ is in the para position.

16. The composition of claim 14, wherein the functional group is an epoxy group.

17. The composition of claim 14, wherein Z is selected from the group consisting of a tertiary amine, a secondary amine, a primary amine, —SH, and —OH.

18. The composition of claim 14, wherein Z is a tertiary amine.

19. The composition of claim 14, wherein L is a 1 to 20 carbon skeleton having 0 to 10 heteroatoms.

20. The composition of claim 14, wherein L is —NC(=O)—Y—
wherein Y is a 1 to 20 carbon skeleton having 0 to 10 heteroatoms.

21. The composition of claim 20, wherein L is a straight chain.

22. The composition of claim 21, wherein Y is selected from the group consisting of alkyls, amidos, carbonyls, ethers, and thioethers.

23. The composition according to claim 14 and having the formula:

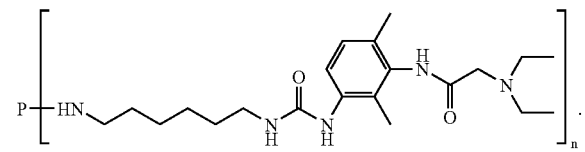

24. The composition according to claim 14 and having the formula:

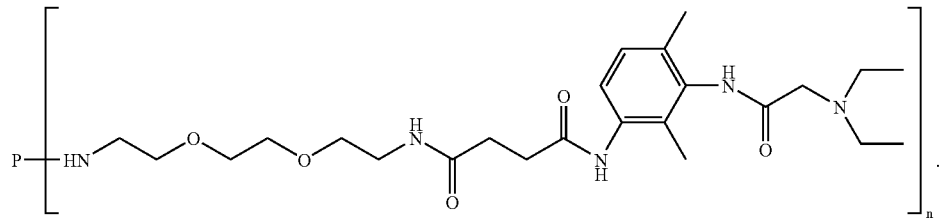

25. A method for detecting the presence or amount of an analyte in a sample, the method comprising:
- contacting the sample with a specific binding pair, the specific binding pair including a first specific binding member and a second specific binding member which are capable of associating with each other to form a complex, the second specific binding member also being specific for the analyte;
- measuring the amount complex formed; and
- determining the presence or amount of analyte based upon the measured complex, wherein the first specific binding member comprises a composition of the formula of claim 14.

26. A method of conducting an immunoassay using the polymer-bound lidocaine analog of claim 14, comprising the steps of:
   a) preparing a solution comprising said polymer-bound lidocaine analog;
   b) adding a test sample containing an unknown concentration of lidocaine to said solution;
   c) adding an anti-lidocaine antibody to said solution;
   d) observing a change in solution turbidity following antibody addition.

27. The method of claim 26, further comprising the step of determining the concentration of lidocaine in the test sample by comparing the change in solution turbidity to a standard curve showing the dependence of a change in solution turbidity on the concentration of lidocaine in a standard solution, said standard solution having a known concentration of lidocaine.

28. A kit for use in performing an immunoassay comprising, in combination:
   1) a composition according to claim 14; and
   2) an antibody specific for the composition and for lidocaine or a derivative thereof.

* * * * *